United States Patent
Williams

(10) Patent No.: US 7,344,674 B2
(45) Date of Patent: Mar. 18, 2008

(54) REMOVABLE AND REUSABLE VACUUM MANDREL AND METHOD FOR MAKING MOLDS AND ORTHOTIC AND PROSTHETIC MEDICAL DEVICES

(75) Inventor: Joseph P Williams, Nashua, NH (US)

(73) Assignee: Atlantc Rim Brace Manufacturing Corp., Nashua, NH (US)

( * ) Notice: Subject to any disclaimer, the term of this patent is extended or adjusted under 35 U.S.C. 154(b) by 843 days.

(21) Appl. No.: 10/458,356

(22) Filed: Jun. 9, 2003

(65) Prior Publication Data

US 2003/0234474 A1 Dec. 25, 2003

Related U.S. Application Data

(60) Provisional application No. 60/390,099, filed on Jun. 19, 2002.

(51) Int. Cl.
*B29C 43/02* (2006.01)
(52) U.S. Cl. ........................ 264/553; 264/222
(58) Field of Classification Search ............... 264/553, 264/222; 24/591.1, 572.1, 573.11
See application file for complete search history.

(56) References Cited

U.S. PATENT DOCUMENTS

| 3,345,711 | A | * | 10/1967 | McCarthy | ............... | 24/573.11 |
| 3,871,367 | A |   | 3/1975  | Miller |
| 3,954,931 | A | * | 5/1976  | Helmuth et al. | ............ | 264/571 |
| 4,688,558 | A |   | 8/1987  | Hooper, Jr. et al. |
| 4,723,905 | A |   | 2/1988  | Vassallo et al. |
| 4,820,221 | A |   | 4/1989  | Aubrey |
| 5,074,288 | A |   | 12/1991 | Miller |
| 5,178,921 | A |   | 1/1993  | Whelan |
| 5,370,604 | A | * | 12/1994 | Bernardoni | ................... | 602/27 |
| 5,376,127 | A | * | 12/1994 | Swanson | ..................... | 623/27 |
| 5,376,129 | A |   | 12/1994 | Faulkner et al. |
| 5,756,027 | A | * | 5/1998  | Rothschild et al. | ......... | 264/138 |
| 5,824,111 | A |   | 10/1998 | Schall et al. |
| 5,901,060 | A |   | 5/1999  | Schall et al. |

OTHER PUBLICATIONS

Essex Orthopaedics, http://www.essexorthopaedics.co.uk/page13.html, May 23, 2002, pp. 1-2.
BIOMECHANICS, BioMechanics Desk Reference 2000, http://www.biomech.com/bdr2000/bracesspinal.html, May 23, 2002, pp. 1-7.

(Continued)

*Primary Examiner*—Monica A Huson
(74) *Attorney, Agent, or Firm*—Vern Maine & Associates

(57) ABSTRACT

For making orthotic braces and prosthetic devices, vacuum shaft mandrels and foam workpiece blanks are pre-fabricated to a standard design for repeatable assembly and disassembly. A mandrel is easily installed in a workpiece blank, or reinstalled in a previously made mold body. The mandrel is likewise easily removed from the mold body and returned to stock after the mold is made and the required brace is completed. Mold bodies are storable for reuse with a mandrel of the same design for the next vacuum forming brace making operation. A limited supply of standard size mandrels can thus be used for making and serving any number of mold bodies. One mandrel size accommodates a range of mold sizes.

11 Claims, 6 Drawing Sheets

OTHER PUBLICATIONS

Boston Brace, Body Jacket, http://www.bostonbrace.com/bodyjacket.html, May 23, 2002.
IPOS Orthopedics Industry, Spinal Orthoses, wysiwyg://393/http://www.ipos-orthopedics.com/centralfab/spinal.asp, May 23, 2002.
IPOS Orthopedics Industry, Modelsoft Stockinette, wysiwyg://397/http://www.ipos-orthopedics.com/materials/ms.asp, May 23, 2002.
IPOS Orthopedics Industry, Carbon Reinforcement Tape, wysiwyg://402/http://www.ipos-orthopedics.com/materials/carbontape.asp, May 23, 2002.
IPOS Orthopedics Industry, The development of ipoc@d2000, wysiwyg://404/http://www.ipos-orthopedics.com/acdcam/default.asp, May 23, 2002, pp. 1-3.
IPOS Orthopedics Industry, Central Fabrication Services, wysiwyg://443/http://www.ipos-orthopedics.com/centralfab/default.asp, May 23, 2002, pp. 1-3.
PCT International Search Report dated Sep. 22, 2004 of International Application No. PCT/US03/19734 filed Jun. 6, 2003.

* cited by examiner

REMOVABLE AND REUSABLE VACUUM MANDREL AND METHOD FOR MAKING MOLDS AND ORTHOTIC AND PROSTHETIC MEDICAL DEVICES

RELATED APPLICATIONS

This application claims the benefit of U.S. Provisional Application No. 60/390,099, filed Jun. 19, 2002.

FIELD OF INVENTION

The invention relates to the making of orthotic and prosthetic medical devices using positive molds and vacuum forming techniques, and in particular to the use of removable and reusable vacuum mandrels in the fabrication of the positive molds upon which open-ended type orthotic devices including spinal, knee, and thigh braces and closed-ended type prosthetic devices are made by vacuum forming.

BACKGROUND OF THE INVENTION

It is well known to make open-ended type orthotic devices including spinal, knee, and thigh braces and closed-ended type prosthetic devices by vacuum forming a thermal plastic sheet on a positive mold. The mold is configured for surface suction of the thermal plastic sheet into conformance with the contours of the mold surface as vacuum is applied to the mold from a vacuum source connection at one end of the mold.

The prior art technique for making the mold provides a shaft, to which is applied a bulk material that can be formed to match the profile of the subject for which a brace is to be made, the shaft ends protruding from the mold end or ends for handling. In one known method, a heavy foam or plaster body is cast as a male mold or mold blank onto a solid shaft so as to encapsulate the shaft and lock the shaft in a non-rotating manner within the mold, the shaft extending out at least one end for handling and fixed or rotating support. For brace making, the shaft is inserted into the throat of a vacuum source, and into a chuck for support and rotation. An orthotic brace or prosthesis is then molded by wrapping thermoplastic sheet material around the mold, extending over the shaft end to and around the vacuum source so as to form an envelope of the thermoplastic sheet material over the mold. The brace is cooled for hardening, and removed from the mold by known methods. The mold is then typically stored for making similar size braces, with or without recontouring of the surface.

In this method, the shaft is committed for the life of the mold and is recoverable only when the mold body is destroyed. Further, a relatively large vacuum pressure is required during the vacuum forming process under this method. The shaft is a relatively expensive component of the mold, compared to the mold body.

In another known method, a plenum or chamber structure of some sort is applied to or fabricated on a hollow shaft or mandrel as a first step. The shaft sidewall is predrilled with small ports along the center section to permit a vacuum source connectible to the shaft end to draw a vacuum within the plenum. A heavy foam or plaster body is then cast as a male mold or mold blank onto the shaft and plenum assembly so as to encapsulate the plenum and lock the shaft in a non-rotating manner within the mold, the shaft ends extending out both ends of the mold for handling and fixed or rotating support. Multiple small diameter holes are drilled through the body of the mold to provide air passageways from the surface to the chamber or plenum. Thermoplastic sheet material is wrapped around the mold body, and with vacuum applied to the shaft end, the sheet material is drawn into conformance with the contours of the mold body. The mold is then stored for reuse for similar size braces, with or without re-contouring of the surface.

This method increases the efficiency of the vacuum forming process, vacuum pressure is significantly reduced extending the life of the vacuum source equipment. However, in this method, as in the prior method, the shaft is committed for the life of the mold and is recoverable only when the mold body is destroyed. As in the above method, the shaft and plenum component is a relatively costly part of the mold. The chamber or plenum portion is usually destroyed with the mold body and not recoverable; only the bare shaft being recoverable for reuse.

In yet another known method, typically a foam mold blank is preformed according to various sizes within which a center hole is bored out to accept the exact shape of a milling machine mandrel. A one or two piece solid shaft mandrel is inserted into the preformed hole in the foam blank, securing it for chucking in a milling machine and milling a surface contour according to a CAD/CAM program so as to create the desired mold. The subsequent vacuum forming process for making a brace is similar to the first prior art technique described above where the shaft end is inserted in the throat of a vacuum source connector flange and chucked for rotation. The thermoplastic material is arranged wrapped by rotation of the mold so as to cover the mold and to extend from the mold to the vacuum source throat to connect the envelope to the vacuum source. The brace is removed as usual. However, in this latter method, the solid shaft milling machine mandrel is removable and reusable, and the mold is storable for reuse without the shaft.

A production brace making operation, commonly called central fabrication, requires the accumulation and use of a large library of molds of varying sizes, in order to provide quick response to medical requirements for spinal braces. Typically, upon receipt of a brace order, a same or similarly sized mold is selected from the library quickly reconfigured to conform to the patient's measurements and used to make the new brace. A new mold is made up when there is no existing mold that can be used as is or can be easily modified or re-contoured to satisfy the requirement, or when a brace is fabricated according to a digitized cast of the patient, which is not readily associated with the traditional format for characterizing and cataloging mold profiles.

Useful context for understanding the art and the invention may be obtained from the following disclosures; U.S. Pat. No. 3,871,367, U.S. Pat. No. 4,688,558, U.S. Pat. No. 4,820,221, and U.S. Pat. No. 5,074,288.

BRIEF SUMMARY

It is therefore a goal of the invention to introduce a lower cost method for making and using positive molds for open ended orthotic medical devices and closed-ended prosthetic devices.

It is also a goal of the invention to have a standard design vacuum mandrel and mold body interface that can be repeatedly assembled and disassembled so that the mandrel is available for use with any mold body having the same interface design.

It is another goal to provide a positive mold assembly for making orthotic devices and prosthetic devices where the mold body is separable from its vacuum mandrel and storable for later reassembly, reworking and use for vacuum forming of additional orthotic and prosthetic devices.

It is yet another goal to prefabricate and configure a workpiece blank for a positive mold, that will accept installation of a compatible design vacuum mandrel in a manner that eliminates the need to fabricate or install a discreet plenum structure on the mandrel over which the mold body must then be applied.

It is a yet further goal to configure vacuum mandrel shafts and mold blanks with a standard interface design enabling simple, non-destructive, repeatable, removal and installation of a mandrel in a mold blank or in a finished mold made from such a mold blank so as to have a limited number of mandrels available for use with any larger number of existing molds and new mold blanks of the same interface design.

It is a still yet further goal to combine an air permeable mold blank with a vacuum mandrel by means of a standard interface design enabling simple, non-destructive, repeatable, removal and installation of a mandrel in a mold blank or in a finished mold made from such a mold blank, without the need for providing an intermediate structural component as plenum about the shaft or within the mold blank.

It is still another goal to have a limited range of progressively sized of vacuum mandrel shaft diameters, preferably three, and mold blanks where each mandrel size and corresponding mold blank size provides a range of possible mold sizes, such that a full range of mold sizes and corresponding brace sizes can be produced.

It is a further goal of one embodiment of the present invention to provide a standard interface design with easily managed components that slide on the mandrel shaft and can be secured so as to grip the mold end or ends with a compliant sealing surface to facilitate the maintenance of a vacuum within the mold core extending to the contoured surface area of the mold.

It is a further goal of another embodiment of the present invention to provide means for anchoring the distal end of a mandrel shaft within a mold blank for single end shaft handling and fabrication of the mold.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
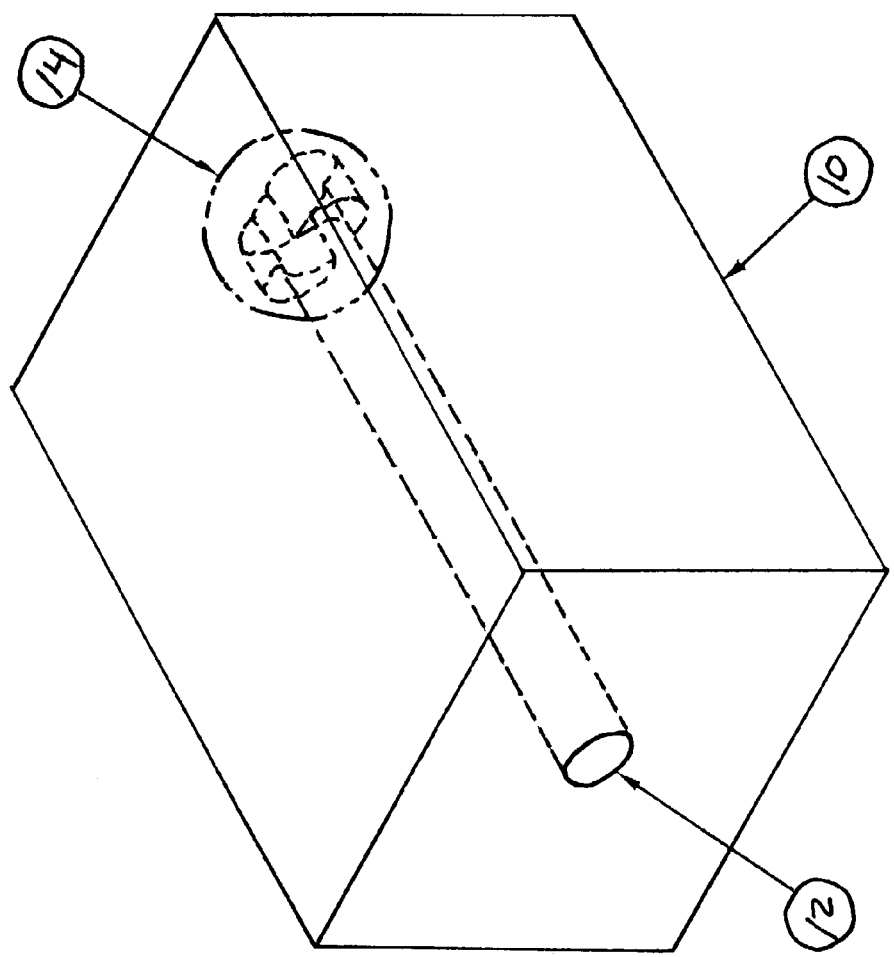
FIG. 1 is a perspective view of a workpiece blank prepared according to one embodiment of the present invention with a bore and a keyed drive recess shown in dotted lines.

The vacuum mandrel and method of the invention departs from the prior art in that the mandrel functions as: (1) a standard interface tool for mounting a workpiece blank configured with a mating standard interface thereupon for handling; (2) a mandrel for holding the workpiece blank in a milling machine to produce a mold shape; (3) a mold holder stem and gripping handle during manual mold modification processes; (4) a vacuum manifold during a vacuum forming process conducted on the mold for making braces and the like; and (5), in particular, as a removable component of a workpiece blank or finished mold assembly so as to permit storage of the mold for later re-use, and use of the mandrel with other and additional workpiece blanks and finished molds, thereby reducing the number of required mandrels and making storage of the molds easier.

Multiple mandrels and mold blanks are pre-fabricated to a standard design for repeatable assembly and disassembly. A mandrel is easily installed in a mold blank, or reinstalled in a mold body of the same mating design. The mandrel is likewise easily removed after the mold is made and/or the vacuum forming process of making a device is completed. Mold bodies are storable for reuse one or several times, at which time a mandrel of the same interface design is reinstalled for the brace making operation. A limited supply of standard size mandrels can thus be used for making and using any number of mold bodies. One mandrel size accommodates a range of mold sizes. A set of 2 to 4 graduated mandrel sizes, preferably 3 sizes, easily provides for a full range of mold sizes for devices ranging from infants to large adults.

Vacuum forming in accordance with the invention requires means for drawing air from the surface of the mold to the bore. Porous or air permeable materials, drilled holes, tubes, sectioned or slices of mold material with corrugated or grooved surface interfaces, or combinations of these, and such other practical or commonly known or used means as are compatible with the invention for directing the entrapped air within the thermoplastic envelope to the bore to be evacuated through the hollow mandrel, thereby conforming the thermoplastic material to the mold contours, are within the scope of the invention. Examples of materials used as mold bodies include but are not limited to rigid open and closed celled foams such as expanded polystyrene, polyurethane, and polyisocyanurate foam. Unlike the prior art, the vacuum mandrel of the invention does not become encapsulated within the body of the mold in the fabrication process.

According to one embodiment of the method of the invention, a relatively porous or air permeable foam block or blank through which air can be readily and uniformly drawn without extra drilled passageways, is the mold blank or workpiece which is fabricated to be assembled with the mandrel and from which the mold body is then fabricated.

An alternate embodiment uses a relatively non-porous foam blank such as a polyurethane foam block, through which holes must be made to provide for applying the vacuum suction to the surface of the mold. Further, with either embodiment, in some cases it may be desirable to cover the mold body with a plaster wash coating, through which holes must be made for the same reason.

A hole boring machine is used to bore out an oversize hole through the center of the workpiece blank, which functions in part as a plenum for the vacuum function. The same boring machine is then offset from the centerline of the blank and applied to a limited depth to create an oversize keyhole or key slot extending outward on one or two sides of the bore in one end of the soft material. The keyhole is configured to mate closely with a key structure on either end assembly of the mandrel so as to enable a non-rotatable assembly of the workpiece to the mandrel. The size of the boring bit, bore and key slot are selected to fit a suitable size mandrel from among the preferably three standard sizes available, based on the length and diameter of the mold. Other keyed mating designs assuring a non-rotating attachment of the mold blank to the mandrel are within the scope of the invention.

The keyed recess extending from the bore as described herein is one method for assuring a non-rotational attachment of the mandrel to the workpiece or mold. Other means for assuring the non-rotational attachment are within the scope of the invention, such as for example, an end plate component to a mounting assembly where the plate has piercing tines that penetrate the end face of the workpiece outboard of the bore diameter when the mandrel is installed in the workpiece or mold.

For double open-end type devices, the mandrel is inserted into the hole in the workpiece aligning the key slot to the key and centering the workpiece bore on the mandrel fixed end chuck and gasket. A removable gasket, centering guide and stop collar are installed on the other end of the mandrel to hold the workpiece in place. The mandrel extends from both ends of the workpiece for the reasons described.

Pressure is applied to the adjustable stop collar to compress the gaskets at each end against the workpiece creating seals at each end of the bore through the workpiece, and the stop collar is secured in position. The seals created by the stop collar gasket and the adjustable collar gasket against the workpiece provide an internal vacuum chamber or plenum within the workpiece.

The mandrel shaft is a hollow tube, plugged at one end and configured with the necessary fittings to connect to a vacuum source at the other end. Ports or holes in the center section of the shaft enable air to be conducted from the surface of the mold, through the porous mold material or holes, through the sealed mold body plenum or core chamber, into the shaft and to the vacuum source. It will be readily apparent that either or both ends could be used for the vacuum connection according to various embodiments.

The assembled vacuum mandrel and workpiece blank are placed in the chuck of the computer controlled milling machine, supporting one or both ends of the mandrel. The mold is formed by automated surface carving or abrading of the foam material according to the particular mold and brace profile required for that order, which is downloaded to the milling machine from the CAD software.

As one skilled in the art would readily appreciate, the mounting assemblies may be positionally adjustable along the mandrel by simply sliding along the mandrel shaft, and secured in position with set screws and the like, as is apparent from the figures. Alternatively, one or both ends of the mandrel may be threaded, with mounting assembly components similarly tapped for rotating advancement along the mandrel, and secured in position with lock nuts or with lock screws against a flat side of the mandrel, or by other means known in the art.

Alternative embodiments are configured to provide a male mold for a prostheses or orthotic appliance having only one open end. In this embodiment, the mandrel is inserted into a bore extending only part way through the body of the workpiece blank. The mandrel is then fixed in place and the workpiece is machined to the proper configuration for the patient.

There are several commercially available software programs for the industry; such as TRACERCAD™ at www.tracer.com, BIOSCULPTOR™ at boisculptor.com, CAPOD™ at www.capod.com, IPOS NORTH AMERICA™ at www.ipos-orthopedics.com, OTTO BOCK™ at www.ottobockus.com, VORUM RESEARCH CORPORATION™ at www.vorum.com, and others. Applicant makes no claim to any software or to any of these trademarks.

As explained, the vacuum mandrel protruding from one or both ends of the mold assembly serves as one or a pair of handles and support points for the milled mold to undergo manual mold modifications (i.e. not done within the CAD software). During a vacuum forming process to make a device, the mandrel end is connected to a vacuum source, the mold is fixed or rotated under manual control, and a hot thermal plastic brace sheet material is applied to the mold. Typically the mold is first wrapped in a mesh or stocking-like fabric material for thermal and physical protection as well as uniform surface distribution of the vacuum effect. As discussed above, a variety of different alternatives are available to distribute the vacuum around the mold and to thereby conform the thermoplastic to the mold. The plastic brace material is then applied as a hot wrap while the mold is fixed or rotated to receive it. The hot plastic sheet is conformed to the mold by manual dexterity and by suction through the porous mold block or drilled holes and stocking layer from the vacuum source connected to the mandrel, and then allowed to cool.

The vacuum formed brace casing is released from the mold for final finishing and shipment. The vacuum mandrel is easily disassembled from the mold body, the mold body is inspected, inventoried and stored, and the mandrel is inspected and returned to stock to be available for making the next new mold body or for assembly to the same or another existing mold body for vacuum forming another brace. As explained, it is preferred to select from the cataloged inventory of usable mold bodies an existing mold body closely conforming to a new brace requirement. It is inspected, assembled with a mandrel from stock, and reworked within limits for making the required brace. If there is no suitable mold in inventory, a new mold is required.

Referring to FIG. 1, there is shown a workpiece 10, a solid porous foam block or blank, through which a bore 12 of about three inches has been made through the long dimension. One end of bore 12 has been further configured with a keyed drive recess 14, which provides for non-rotational engagement with a suitable drive shaft component. The block is oversize with regard to cross section as compared to a required orthotic brace for a human torso.

Figure 2:
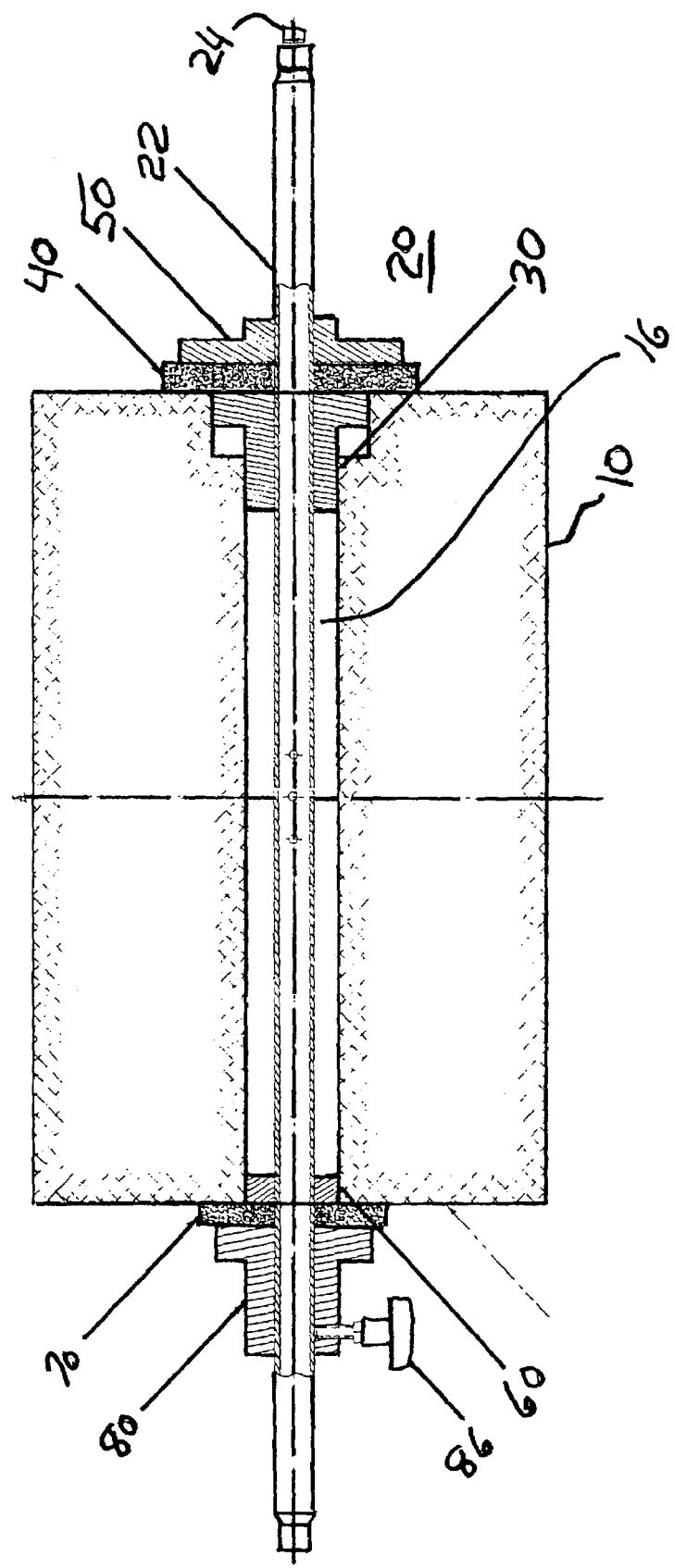
FIG. 2 is a sectional view of a workpiece and vacuum mandrel configured and assembled in accordance with one embodiment of the present invention.
Figure 3:
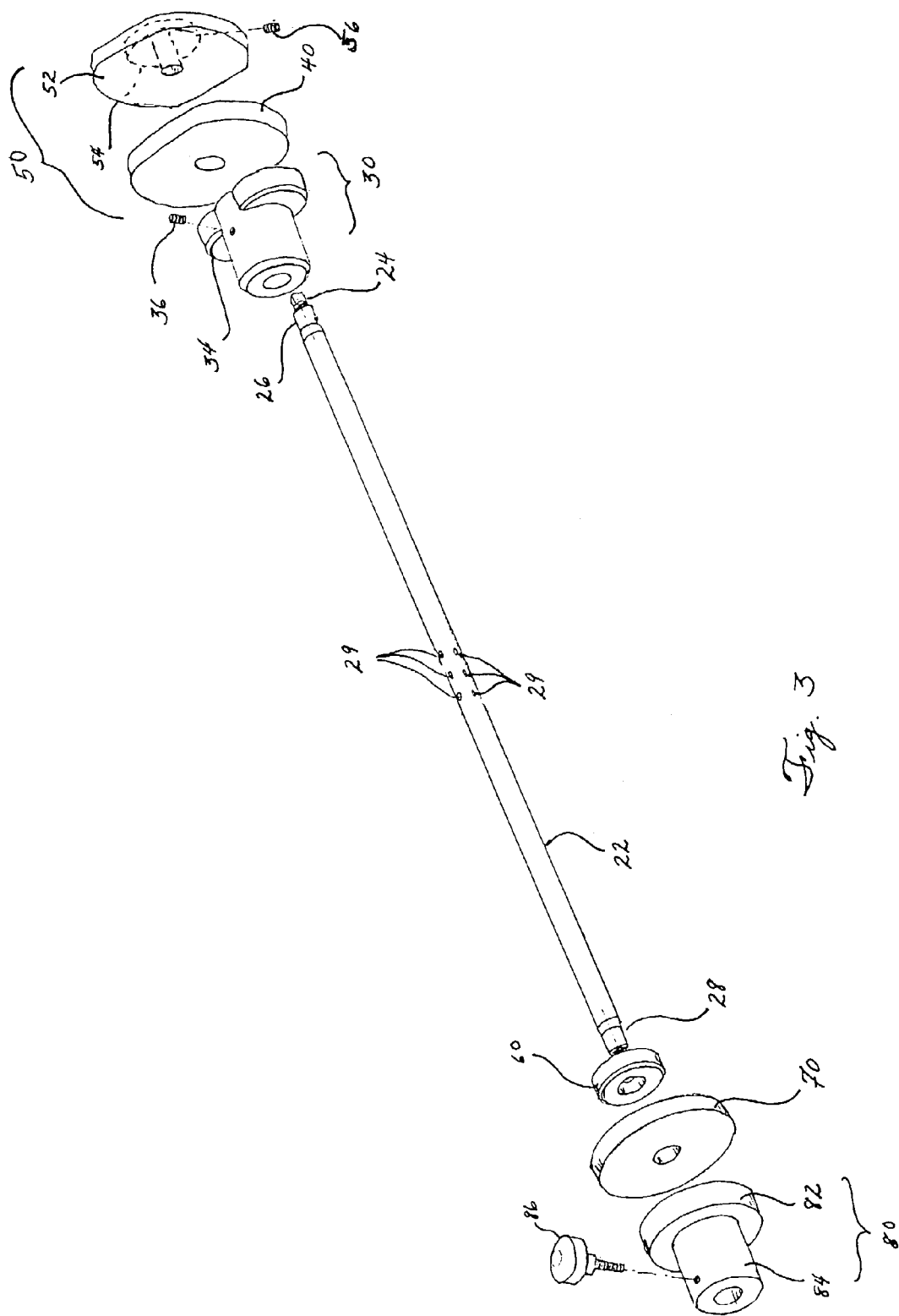
FIG. 3 is a perspective view of vacuum mandrel configured in accordance with one embodiment of the present invention, illustrating the various components thereof.

Referring to FIGS. 2 and 3, the workpiece of FIG. 1 has been installed on vacuum mandrel assembly 20, and is ready to be installed in a computer operated sizing machine for reduction to the required mold size for the orthotic brace. Vacuum mandrel assembly 20 consists of vacuum mandrel shaft 22, which is hollow with a cap 24 on the keyed drive end 26; the other end referred to as the adjustable end 28 and being connectable to a vacuum source so as to provide suction at vacuum ports 29.

Referring to FIGS. 2—and 3, at the keyed drive end of mandrel shaft 22 there is a key drive end assembly of components including from inboard to outboard on the shaft, a key drive collar 30, stop collar gasket 40 and stop collar 50. These components are arranged and secured on shaft 22 prior to the installation of workpiece 10 over the adjustable end of shaft 22.

Key drive collar 30 consists of a bore size section with a tapered end which will accept and center the workpiece by its bore 12, and a key drive section 34 with a tapered end which will with proper rotational alignment accept the key drive recess 14 so as to hold workpiece 10 in a non-rotational fit. Key drive collar 30 is secured to shaft 22 by set screw 36. Adjacent key drive collar 30 is stop collar gasket 40, a compressible seal that is larger than keyed drive recess 14 so as to contact the end face of workpiece 10 when it is installed. This provides a relatively soft grip on the end face of the workpiece and a vacuum seal to bore 12. Gasket 40 is supported by stop collar 50, which has a supporting flange section 52 of about the same size as gasket 40, and an outboard collar section 54 through which set screw 56 is applied to shaft 22. It will be apparent that the length of keyed drive recess 14 is sufficiently greater than the length of key drive section 34 to enable the required compression of gasket 40 by workpiece 10 against stop collar 50 without bottoming out of the key in the recess.

Referring now to FIGS. 2 and 3, there is provided for securing a workpiece 10 onto shaft 22, an adjustable end assembly of components consisting of from inboard to outboard on shaft 22; a centering guide collar 60, a compressible collar gasket 70, and an adjustable end collar 80. Centering guide collar 60 has a tapered inboard end for insertion into bore 12 of the workpiece. Gasket 70 is sized to contact the end face of workpiece 10 and vacuum seal bore 12. Adjustable end collar 80 has a supporting flange section 82 for supporting gasket 70, and an outboard collar section 84 through which locking knob 86 is operated to secure end collar 80 to shaft 22.

With the keyed end components 30, 40, and 50, secured to shaft 22, workpiece 10 is then aligned and installed over adjustable end 28 onto shaft 22 so as to place keyed drive recess 14 of the workpiece into position on key drive collar 30 and into contact with gasket 40. The adjustable end components 60, 70, and 80 are then installed on adjustable end 28 of shaft 22 and centered on the workpiece so as to hold it suspended around shaft 22. Adjustable end collar 80 is advanced towards key end collar 50 until gaskets 40 and 70 are suitably compressed, and then locked into position on shaft 22 with locking knob 86. The resulting structure provides a vacuum mandrel shaft servicing a plenum 16 formed by bore 12 of the workpiece and gaskets 40 and 70.

For closed-ended type devices, the procedure is similar to that described above. However, in such an embodiment, the bore is configured to extend only partially through the center of the workpiece blank, either by limited penetration of the boring device or by use of an end cap of the same material applied with adhesive over one bore end. The open end of the bore may be further configured with a key slot as described above. The mandrel is inserted in the open end and the distal end supported at the far end of the bore by any of several means described below. A centering guide or keyed centering guide on the proximate end of the mandrel provides radial support on the near end of the workpiece. A gasket seals the near end of the workpiece, facilitating the vacuum molding process.

Figure 4:
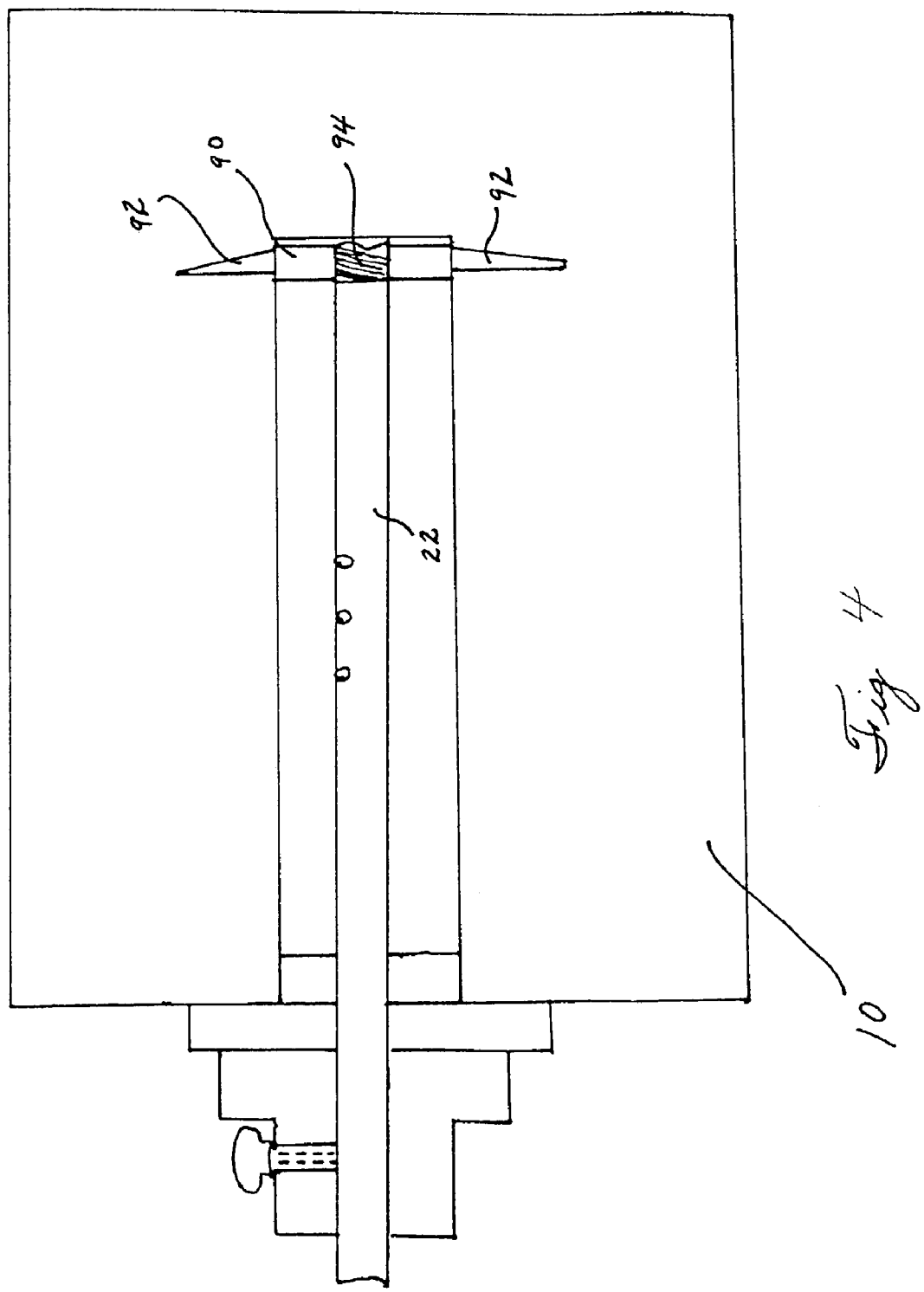
FIG. 4 is an elevation section view of a workpiece blank and vacuum mandrel wherein the workpiece blank has only one open end configured according to one embodiment of the present invention having an insertable, internal shaft end support with deployable end anchors shown deployed.
Figure 5:
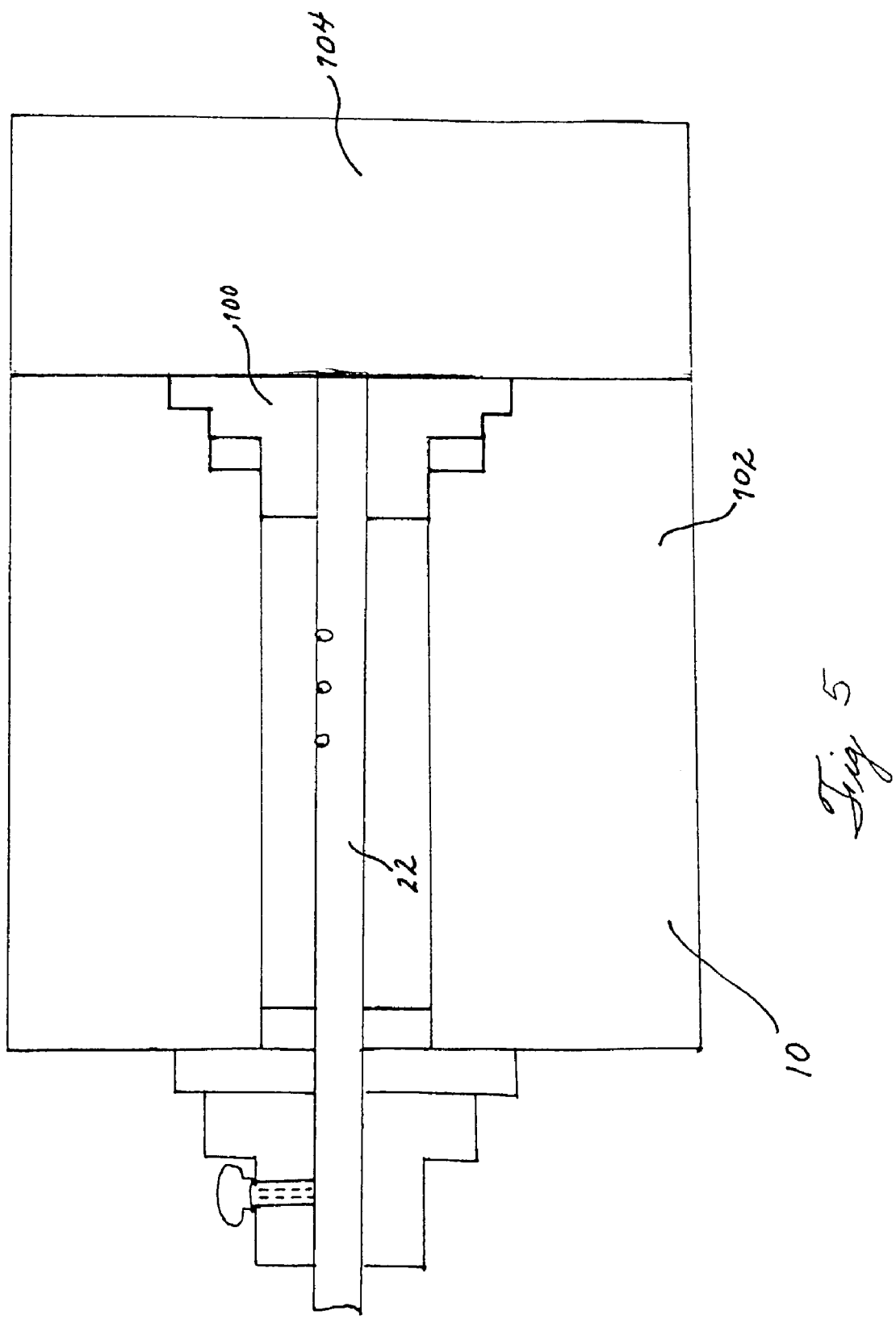
FIG. 5 is an elevation section view of a workpiece blank and vacuum mandrel wherein the workpiece blank has one open end configured according to another embodiment of the present invention, and a workpiece end cap applied to the other end so as to cover a keyed mandrel stop with a contourable surface area.
Figure 6:
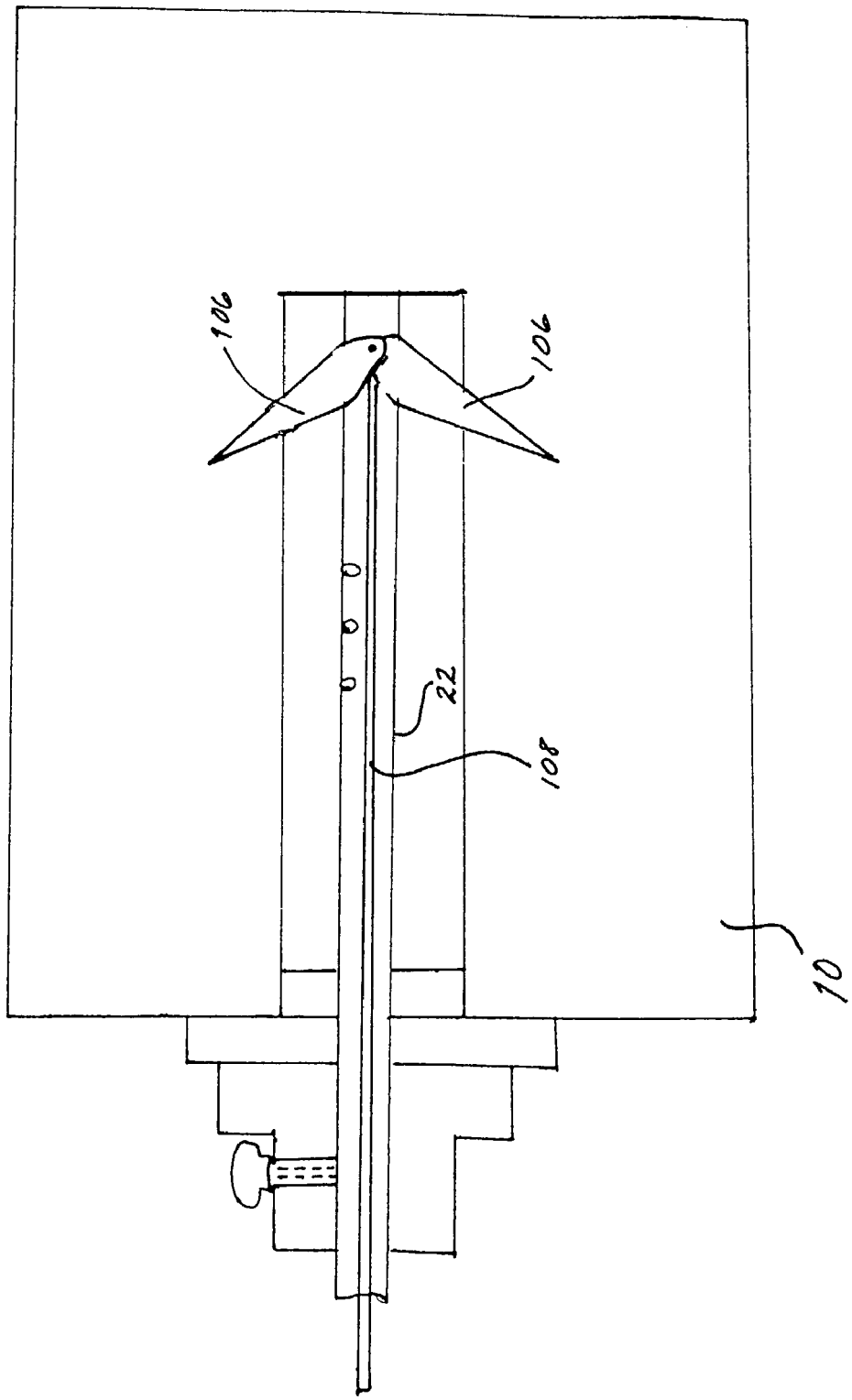
FIG. 6 is an elevation section view of a workpiece blank and vacuum mandrel wherein the workpiece has only one open end configured according to a further embodiment of the present invention, and the mandrel has a retractable anchor mechanism at its distal end for internal anchoring within the workpiece bore.

As one of ordinary skill in the art will readily appreciate from FIGS. 4-6, a variety of fixation methods can be used to mount the mandrel 22 in the workpiece blank 10 for male molds for the production of orthotic braces and prostheses having only a single open end. In one embodiment, illustrated in FIG. 4, a permanent anchor 90 with radially extendible flukes 92 can be inserted with the mandrel into the bored hole 12, and the flukes 92 then expanded by various rotational or lever actuated means, locking the anchor 90 into the workpiece 10. This anchor remains in the workpiece 10 until the workpiece 10 is destroyed. Once this anchor 90 is fully bedded or fixed within the workpiece 10, the mandrel 22 may be retracted by means of a threaded joint or other known shaft locking mechanism 94 between the mandrel 22 and the anchor 90, and re-inserted again as required.

Alternatively, as illustrated in FIG. 5, other embodiments may incorporate an anchor 100 configured in a keyed geometry as in the open ended embodiment, prior to the attachment of an end cap 104 over the bore 12. The anchor 100 is embedded in the distal end of the main or first section of work piece 102, and the work piece cap or second section of the workpiece 104 is then securely affixed, preferably with a suitable adhesive, over the end of the main section 102 and the anchor 100, effectively locking the anchor 100 within the body of the workpiece 10. The mandrel 22 can then be inserted and made fast in the workpiece 10 as described in the previous embodiment.

As illustrated in FIG. 6, the mandrel 22 itself can be configured with hinged flukes 106 as a self anchoring device. Anchor flukes 106 can be configured to be extendable and retractable, articulated by a lever or other mechanism 108 in such a way that each time the mandrel 22 is retracted from the bore 12, no part is left inside the workpiece 10.

When the mold is used for the molding of a prosthetic device, the finished, close ended mold, designed to match the shape of the individual patient's residual limb or stump, may be oriented vertically, with the open end of the bore oriented downward. A vacuum is applied by a vacuum source attached to the mandrel. The mold is mounted on the mandrel, a seal, through which the mandrel is inserted is in contact with the mold, effectively closing the open end of the bore. A thermoplastic sheet is formed over the mold, thereby forming a socket for receiving a residual limb or stump. Additional finishing and assembly may be applied to the socket as necessary to complete the prosthetic device. The force from the vacuum and the weight of the mold hold the mold securely against the seal, and prevent displacement of the mold during the process of forming. In this embodiment, less force is required from the mounting system than in other, horizontal, embodiments to maintain a proper seal for the vacuum to function effectively. The mounting mechanism, however, must be of adequate strength to withstand the mold fabrication process. Alternatively the mounting mechanism may be of sufficient strength to assist the user in the removal of the mold from the finished prosthetic device.

With the mandrel non-rotatably installed in the workpiece blank, the preferably porous workpiece and vacuum mandrel assembly are now ready for the mold making and brace making process as described above. In the case where the workpiece consists of a non-porous material, or if a non-porous surface treatment is applied to the mold, air holes may be drilled into bore 16 to realize the required suction at the surface for molding the brace in the manner known in the art.

Upon completion and release of the required orthotic brace, the vacuum mandrel assembly 20 is removed from the finished mold that was workpiece 10, to be available for use with another workpiece or mold, or for later reinstallation in the existing mold for making another brace, all as described above.

The manual removal procedure for removing the mandrel from the workpiece is quite simple. It is described here for a double ended mold with shaft locking assemblies exposed at either end. In this embodiment, referring to FIG. 3, one end of the shaft is the keyed end as previously described, normally fixed in position on the shaft, and the other end is described as the adjustable end. At the adjustable end, locking knob 86 is loosened and adjustable end collar 80, and gasket 70, are removed from the mandrel shaft. The shaft with its keyed end components still secured to the shaft, is then loosened and partially withdrawn through the bore towards the drive key end of the mold body until the shaft is withdrawn from centering guide 60. The shaft can then be tilted slightly and used to push the centering guide 60 out of the other end of the mold body bore. The shaft with its keyed end components is then fully withdrawn from the mold body. The adjustable end components of the vacuum mandrel assembly are then reassembled to the shaft, and it is returned to stock for reuse.

Other and various configurations for removably and non-rotatably locking the workpiece to the shaft are within the scope of the invention, so long as the vacuum mandrel assembly may be removed from and replaced within the mold in a manner that is substantially non-destructive of the workpiece bore. Examples of such locking configurations include but are not limited to pneumatic bladders or friction surfaces that resist the withdrawal of the mandrel from the central bore. As will be readily apparent to those skilled in the art, some interchanging and manipulation of locking assemblies and anchoring devices may be necessary to use standard mandrels with every variation of workpiece and mold interface. Variations to the basic embodiment permit an eventual oversize re-boring and recessing of the workpiece to a next larger size mandrel after multiple uses may have worn the bore, keyed recess, and/or end surfaces beyond useable condition. Alternatively, a degraded or excessively large bore may be filled with foam, allowed to cure, then re-bored. Such a degraded, damaged, or worn bore may be lined with a sleeve inserted in to the bore. Such a sleeve may be comprised of rigid plastic and is, according to one embodiment air permeable. Similar liners or sleeves may be installed in the keyed recesses if necessary. Other aspects of the art as are commonly practiced may be compatible and incorporated with the claimed invention and such equivalents as are within the scope of the law.

One embodiment of the present invention provides a system for the support and control of a vacuum forming male mold, that system comprising a male mold body having a central bore and means for admitting air from the surface of said body to the central bore, a mandrel removably and non-rotatably mounted substantially coaxially with the central bore, the mandrel being hollow and configured to connect to a vacuum source. One skilled in the art will readily appreciate that a wide variety of methods for removably and non-rotatably mounting the mandrel in the central bore are within the scope of this invention. Examples of such methods include, but are not limited to the use of pneumatic bladders to apply pressure to the workpiece, the use of friction between components of the mandrel assembly and the workpiece to resist movement, the application of pressure to the mold with clamps or other mechanical devices. The mandrel has at least one aperture communicating with the central bore. Also forming part of the system are a first gasket whereby said central bore is sealed when said system is in use, and at least one adjustable clamp assembly whereby the first gasket and the mandrel are stabilized and centered with respect to the central bore.

The shaft of the mandrel may be composed of two or more short sections or segments coupled together, either with fittings, tapped or threaded joints, clips, clamps, adaptors or short nipples or other joining methods known to those skilled in the art. Alternatively the shaft may be of unitary construction.

The system of this embodiment may also provide a keyed recess disposed at a first end of said central bore, and a mandrel mounting assembly having a first centering collar and keyed flange, the mounting assembly being non-rotatably attachable to the mandrel, the flange being configured to mate with the keyed recess and prevent rotational movement of the male mold body.

The system configured according to this embodiment may include a second gasket disposed proximate to the keyed flange, and a stop collar configured to compress the second gasket against the male mold body.

The adjustable clamp assembly of this embodiment may comprise: a second centering collar; and an adjustable collar, the centering collar being disposed within said central bore proximate to the first gasket, and the adjustable collar being disposed proximate to an opposing side of the first gasket from the second centering collar, the adjustable collar being configured with positional adjustability along the mandrel for compressing the first gasket against the male mold body.

Another embodiment of the present invention provides a system for the fabrication of a male mold, the system comprising: a computer aided manufacturing system; a mandrel, removably and non-rotatingly, that is, incapable of rotational movement, mountable coaxially within a central bore of a workpiece, the mandrel being hollow and configured to be connected to a vacuum source, and having at least one aperture communicating with the central bore when the mandrel is mounted therein; a chuck, in which a first end of the mandrel is mountable, the chuck configured for controlling rotational movement of the mandrel and the workpiece in accordance with the computer aided manufacturing system; and a machining tool configured for applying desired profile to the workpiece as the work piece is manipulated by the chuck, the profile being produced according to inputs to the computer aided manufacturing system.

This embodiment may also include a mandrel mounting assembly having a first centering collar and keyed flange, the flange being configured to mate with a keyed recess disposed at a first end of said central bore and prevent rotational movement of the workpiece relative to the mandrel.

The system may also provide a second gasket disposable on said mandrel proximate to said keyed flange and a stop collar disposable on said mandrel and configured with positional adjustability along said mandrel whereby said second gasket is compressed against said keyed flange and against said workpiece. It may also include a first gasket disposable on said mandrel whereby the central bore is sealed and at least one adjustable clamp assembly disposable on the mandrel whereby the first gasket and the mandrel are stabilized and centered with respect to the central bore.

Such an adjustable clamp assembly may comprise: a second centering collar; and an adjustable collar, the centering collar being disposable within the central bore proximate to the first gasket, and the adjustable collar being disposable proximate to an opposing side of the first gasket from the second centering collar, the adjustable collar being configured with positional adjustability along the mandrel for compressing the first gasket against and the male mold body.

A further embodiment of the present invention provides a method of using a vacuum mandrel assembly, that method comprising the steps of, inserting a hollow mandrel shaft into a central bore disposed in a workpiece having means for admitting air from the surface of said workpiece to the central bore, the hollow mandrel shaft having at least one aperture communicating with the central bore; centering said hollow mandrel shaft using at least a first centering collar; removably, non-rotatably securing the hollow mandrel shaft within the central bore, that is, mounting the shaft in such a way as to be capable of removing the shaft without damage to the workpiece, but when the shaft is inserted, the shaft is incapable of rotational movement; sealing the central bore with at least a first gasket; and stabilizing the mandrel with respect to the central bore with an adjustable clamp whereby the first gasket is compressed against the workpiece.

In this method, the workpiece may be a workpiece blank, and the method may also include the step of machining that workpiece blank to form a vacuum forming male mold body. Alternatively, the workpiece may comprise a vacuum forming male mold body and the method may further comprising the steps of, placing a heated sheet of thermoplastic material over the vacuum forming male mold; and applying a vacuum source to the hollow mandrel shaft, thereby conforming the thermoplastic material to the vacuum forming male mold body.

Yet another embodiment of the present invention provides a workpiece blank for making a positive mold body, that workpiece blank comprising: a first block of mold material; a central bore extending at least partially through the block, the central bore being of a diameter of adequate size to admit a removable, vacuum mandrel, and a keyed cavity disposed at one end of the bore and configured to mate with a keyed flange on the vacuum mandrel. In such an embodiment, the mold material may be air permeable.

A second block of mold material may be provided, with the bore extending fully through said first block, the first block also having an anchor assembly recess disposed at the other end of the bore, the second block sized for attachment to the first block whereby capping the anchor assembly recess. The block may have at least one hole extending from the surface to the central bore. The block may comprise a material chosen from the group of materials consisting of plaster and foam.

A still further embodiment of the present invention provides a vacuum mandrel assembly for installation and removal from a vacuum forming mold, comprising: a hollow shaft with at least one end configured for attachment to a vacuum source and at least one sidewall aperture for communicating said vacuum source to a central bore in the vacuum forming mold, the vacuum forming mold comprising means for admitting air from the surface of the mold to the central bore; a mounting assembly on a first end of the shaft configured for non-rotational mating to a first open end of a central bore extending at least partially through a the workpiece blank or vacuum forming mold; and a means for releasably securing the second end of the mandrel to the second end of the central bore.

Such a vacuum mandrel is susceptible to a variety of alternative embodiments. The means for non-rotational mating may be a keyed recess in the first end of the central bore, and a matching key on the mounting assembly. The means for securing the second end of the mandrel to the second end of the bore may have a bore centering and locking assembly disposed on the second end of the mandrel. A second mandrel end anchor assembly may be installed within said vacuum forming mold at the second end of the central bore.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

I claim:

1. A method of using a vacuum mandrel assembly, said method comprising:
   removably inserting a hollow mandrel shaft into a central bore disposed in a workpiece having means for admitting air from the surface of said workpiece to said central bore, whereby said hollow mandrel shaft has at least one aperture communicating with said central bore, and at least one end of said hollow mandrel shaft extending from said workpiece with at least one aperture connectible to a vacuum source;
   releaseably, non-rotatably securing said hollow mandrel shaft within said central bore so as to have said workpiece non-rotatingly mounted on said hollow mandrel shaft with said at least one end of said hollow mandrel shaft extending therefrom;
   centering said hollow mandrel shaft within said central bore using at least a first centering collar; and
   making a first vacuum forming male mold body of a desired profile from said workpiece blank.

2. The method according to claim 1, wherein said method further comprises making a first vacuum formed casing conforming to said male mold body by the steps:
   sealing said central bore for vacuum forming with an adjustable clamp on said hollow mandrel shaft whereby a first gasket is compressed against said workpiece;
   placing a heated sheet of thermoplastic material over said vacuum forming male mold body;
   applying a vacuum source to said hollow mandrel shaft, and hence through said central bore to the surface of said vacuum forming male mold body, thereby conforming said thermoplastic material to said vacuum forming male mold body as a said vacuum formed casing;
   removing said casing from said vacuum forming male mold body; and
   unsealing the central bore and releasing and removing said hollow mandrel shaft from said vacuum forming male mold body without damage to the male mold body, whereby said male mold body may be similarly used with another said hollow mandrel shaft and said hollow mandrel shaft may be similarly used with another said workpiece, the same said male mold body or another said male mold body.

3. The method of claim 1, said workpiece comprising:
   a first block of mold material;
   a central bore extending at least partially through said block; and
   a keyed cavity disposed in said central bore and configured to mate with a keyed flange on said hollow mandrel shaft;

said removably, non-rotatably securing said hollow mandrel shaft within said central bore comprising inserting said keyed flange into said keyed cavity.

4. The method of claim 3
said keyed cavity comprising an anchor assembly recess with an anchor affixed therein; said keyed flange on said hollow mandrel shaft comprising a shaft locking mechanism configured for engagement with said anchor; said inserting said keyed flange into said keyed cavity comprising engaging said shaft locking mechanism with said anchor.

5. The method of claim 2 wherein said means for admitting air from the surface of said workpiece to said central bore comprises at least one hole extending from the surface to the central bore, and said applying a vacuum source to said hollow mandrel shaft, and hence through said central bore to said vacuum forming male mold body comprises applying a vacuum source to said hollow mandrel shaft and hence through said central bore and said at least one hole extending from the surface to the central bore.

6. The method of claim 2, further comprising making another vacuum formed casing by the steps:
    inserting a said hollow mandrel shaft into said central bore of said vacuum forming male mold body;
    removably, non-rotatably securing said hollow mandrel shaft within said central bore so as to have said vacuum forming male mold body non-rotatingly mounted on said hollow mandrel shaft with said at least one end of said hollow mandrel shaft extending therefrom; and
    repeating the steps of claim 2.

7. The method of claim 2, further comprising making a second said male mold body by the steps:
    inserting a said hollow mandrel shaft into said central bore of said vacuum forming male mold body;
    removably, non-rotatably securing said hollow mandrel shaft within said central bore so as to have said vacuum forming male mold body non-rotatingly mounted on said hollow mandrel shaft with said at least one end of said hollow mandrel shaft extending therefrom; and
    reworking said vacuum forming male mold body to a desired new profile.

8. The method of claim 7, further comprising making a second said vacuum formed casing by repeating the steps of claim 2.

9. A method of using a vacuum mandrel assembly, said method comprising:
    (1) using a workpiece configured with a central bore extending from one end at least partially there through, said central bore configured with a keyed section, said workpiece further configured with means for admitting air from the surface of said workpiece to said central bore;
    (2) removably inserting a hollow mandrel shaft with a keyed flange into said central bore such that said keyed flange is engaged with said keyed section, said hollow mandrel shaft having at least one aperture thereby communicating with said central bore, and at least one end of said hollow mandrel shaft extending from said workpiece with at least one aperture connectible to a vacuum source;
    (3) centering said hollow mandrel shaft within said central bore using a centering collar and sealing said central bore with a gasket; (4) securing said hollow mandrel shaft to said workpiece by securing an adjustable clamp whereby said gasket is compressed against said workpiece;
    (5) making a vacuum forming male mold body of a desired profile from said workpiece;
    (6) placing a sheet of vacuum formable material over said vacuum forming male mold body;
    (7) applying a vacuum source to said hollow mandrel shaft, and hence through said central bore and said vacuum forming male mold body to the surface thereof, thereby conforming said vacuum formable material to said vacuum forming male mold body as a vacuum formed casing;
    (8) removing said casing from said vacuum forming male mold body; and
    (9) unsealing the central bore and releasing and removing said hollow mandrel shaft from said vacuum forming male mold body without damage to the male mold body, whereby said male mold body may be similarly used with another said hollow mandrel shaft and said hollow mandrel shaft may be similarly used with another said workpiece or another said male mold body.

10. The method of claim 9, further comprising:
repeating steps 2-4 and 6-9.

11. The method of claim 9, wherein said workpiece is a vacuum forming male mold body and step (5) making a vacuum forming male mold body of a desired profile from said workpiece comprises step (5) reworking said vacuum forming male mold body to a new desired profile, said method further comprising:
repeating steps 2-9.

* * * * *